United States Patent [19]

Ishihara

[11] Patent Number: 4,493,707
[45] Date of Patent: Jan. 15, 1985

[54] TUBAGE USED FOR INTUBATION

[75] Inventor: Yoshihisa Ishihara, Hiroshima, Japan

[73] Assignee: Japan Medical Supply Co. Ltd., Hiroshima, Japan

[21] Appl. No.: 482,090

[22] Filed: Apr. 4, 1983

[30] Foreign Application Priority Data

Feb. 10, 1983 [JP] Japan .......................... 58-017476[U]

[51] Int. Cl.³ ............................................. A61M 5/00
[52] U.S. Cl. ................................... 604/164; 604/122; 604/272
[58] Field of Search ............... 604/164, 165, 167, 169, 604/118, 122, 272, 173, 174, 43–45, 53

[56] References Cited

U.S. PATENT DOCUMENTS 3,714,945 2/1973 Stanley ................................. 604/164
4,217,895 8/1980 Sagae et al. ........................... 604/44
4,385,631 5/1983 Uthman ............................... 604/284

Primary Examiner—Stephen C. Pellegrino
Attorney, Agent, or Firm—Lawrence I. Field

[57] ABSTRACT

A tubage for use in an intubation is provided. The tubage comprises a tubular body having a first conduit and a second conduit which are formed therein to extend in a longitudinal direction, a flange portion formed to extend substantially perpendicular to the longitudinal direction and a side hole which is formed in the first conduit at a predetermined distance from the flange portion.

11 Claims, 7 Drawing Figures

FIG. 1
FIG. 2
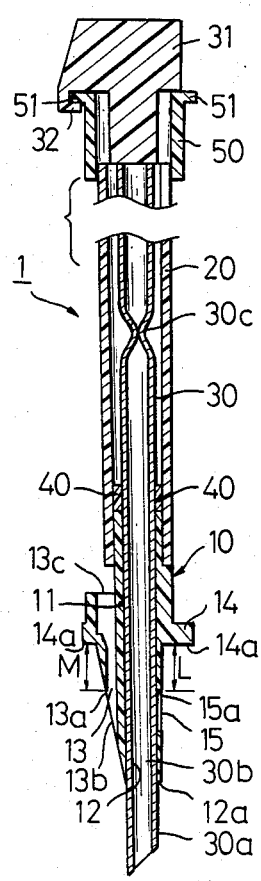
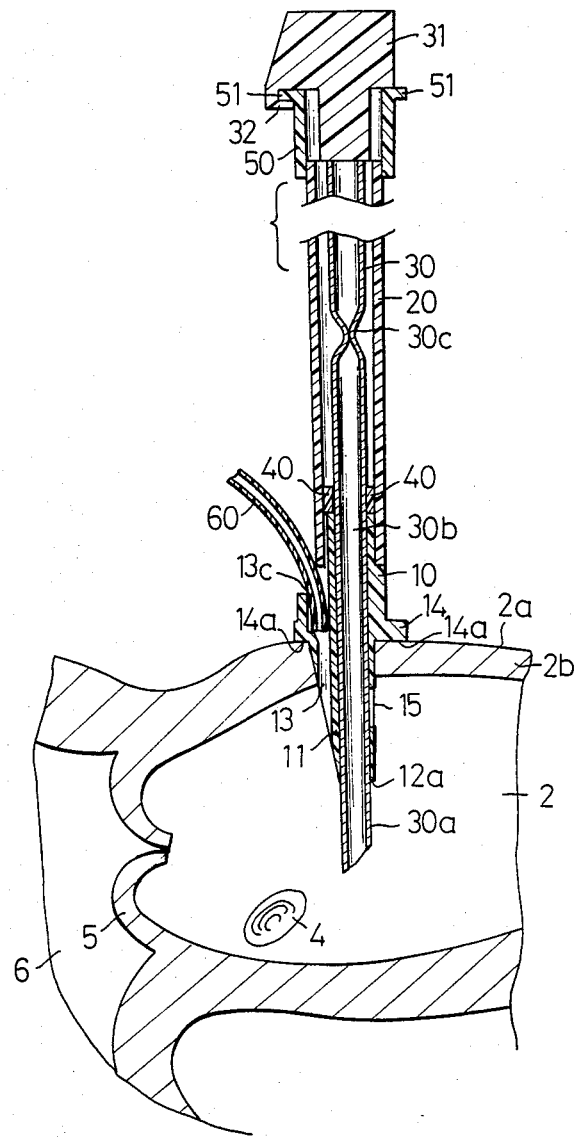

TUBAGE USED FOR INTUBATION

BACKGROUND OF THE INVENTION

The present invention relates to a tubage which is used in an open heart surgery operation in chest surgery, such as valvular substitution, repair of septum repair or the like and, more particularly, to an aortic tubage having a plurality of conduits.

Generally, the open heart surgery operation in chest surgery require various works as follows during the operation.

(i) To remove air bubbles in the heart cavity by air vent needles in order to avoid various accidents which may, for otherwise, be caused by the air bubbles in the blood.

(ii) To inject a cardiac muscle protective liquid to protect the cardiac muscle in the case of aortic atresia or heart stop.

(iii) To measure the artery pressure by means of a dwelling needle for monitoring the function of the heart.

These works require greater number of piercing and cutting of artery and, hence, greater number of suture after the extraction of the needles. This is quite disadvantageous not only for the patient but also for the surgeon because the needles undesirably obstructs the field of vision of the surgeon and because the piercing, cutting and suture require impractically long time.

In addition, the air vent needles, injection needles and dwelling needles, which are usually made of stainless steel, tend to damage the other portions of the aorta than the aimed portions, e.g. the wall of the aorta oposite to the pierced portion of the wall.

SUMMARY OF THE INVENTION

Accordingly, an object of the invention is to provide a tubage for use in various purposes such as extraction of bubbles, injection of aortic atresia protective liquid and measurement of artery pressure in an open heart surgery operation in chest surgery, such as valvular substitution, repair of septum defect and so forth.

Another object of the invention is to provide a tubage which can reduce the number of piercing or cutting to relieve the patient and to eliminate unnecessary circuit thereby to improve the field of vision of the surgeon.

Still another object of the invention is to provide a tubage which is easy to manipulate and improved to permit the surgeon to complete the operation in a shorter period of time.

A further object of the invention is to provide a tubage which is improved to minimize the damaging of the artery wall during the use.

Briefly, according to the invention, there is provided a tubage having a tubular body constituted by a first conduit and a second conduit formed to extend in the longitudinal direction of the tubage body, a flange portion extending in the direction perpendicular to the longitudinal direction, and a side hole formed to open to the first conduit at a predetermined distance from the flange portion.

More specifically, the invention provides a tubage comprising: a first tubular body having a first conduit and a second conduit formed to extend in the longitudinal direction of the tubage body, a flange portion extending in the direction perpendicular to the longitudinal direction, and a side hole formed to open to the first conduit at a predetermined distance from the flange portion; a flexible second tubular body connected at its one end to one end of the first conduit so as to communicate with the first conduit; a hollow needle removably received by the first conduit and by the flexible second tubular body; and a liquid seal means provided between the inner surface of the second tubular body and the outer surface of the hollow needle.

In a preferred form of the invention, the first conduit has a greater diameter than the second conduit, and the flange portion is provided at substantially mid point in the longitudinal direction of the first tubular body, the sbstantially mid point containing the first and second conduits.

According to another preferred form of the invention, the distance between the end surface of the flange and the edge of the side hole adjacent to the flange portion is substantially equal to the distance between the end surface of the flange portion and the open end of one end opening of the second conduit.

The invention accordingly comprises the features of construction, combination of elements, and arrangement of parts which will be exemplified in the construction hereinafter set forth, and the scope of the invention is set forth in the claims appended hereto.

DESCRIPTION OF THE DRAWINGS

A more complete appreciation of the present invention and many of the attendant advantages thereof will be readily understood by reference to the following detailed description when considered in connection with the accompanying drawings in which:

FIG. 1 is an enlarged sectional view of a tubage in accordance with the invention;

FIGS. 2 to 4 are enlarged sectional views illustrating the state of use of the embodiment of the tubage shown in FIG. 1;

DESCRIPTION OF THE PREFERRED EMBODIMENTS

Figure 3:
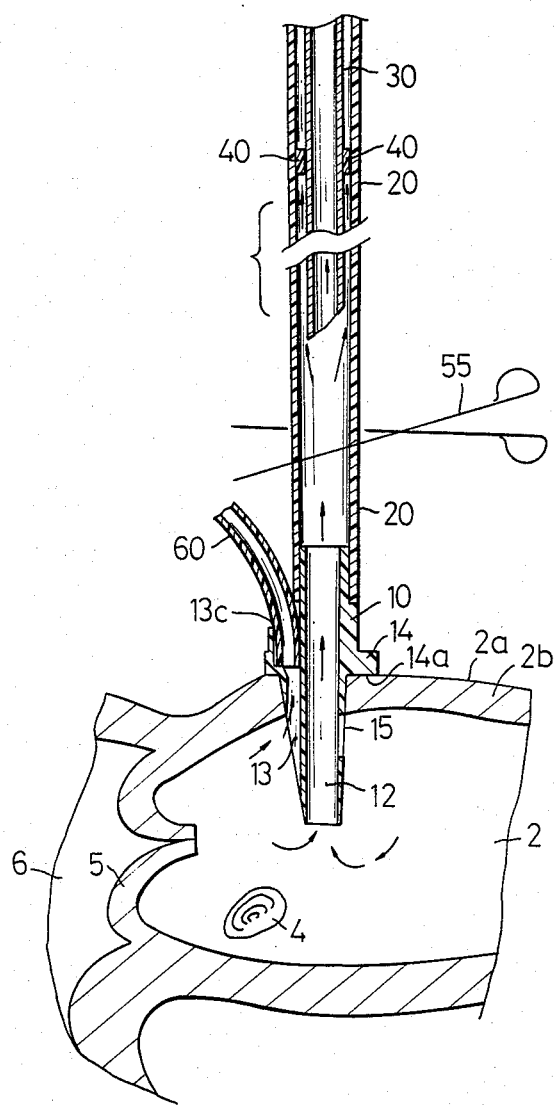
Figure 5:
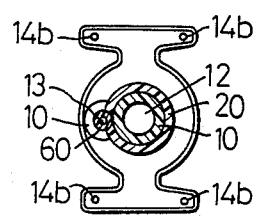
FIG. 5 is a sectional view taken along the line V—V of FIG. 4.

A preferred embodiment will be described hereinunder with reference to the accompanying drawings. Although the description mentions specifically an aortic tubage, it is to be understood that the tubage of the invention can be used equally for veins.

FIG. 1 shows an aortic tubage 1 having a tubage body 10 provided with two conduits 12 and 13, a tube 20 inserted and fixed at its one end to the base end of the tubage body 10, a stabbing guide needle 30 most part of which being received by the tubage body 10 and by the tube 20, and a plug 40 fixed to the outer wall of the stabbing guide needle 30.

Figure 4:
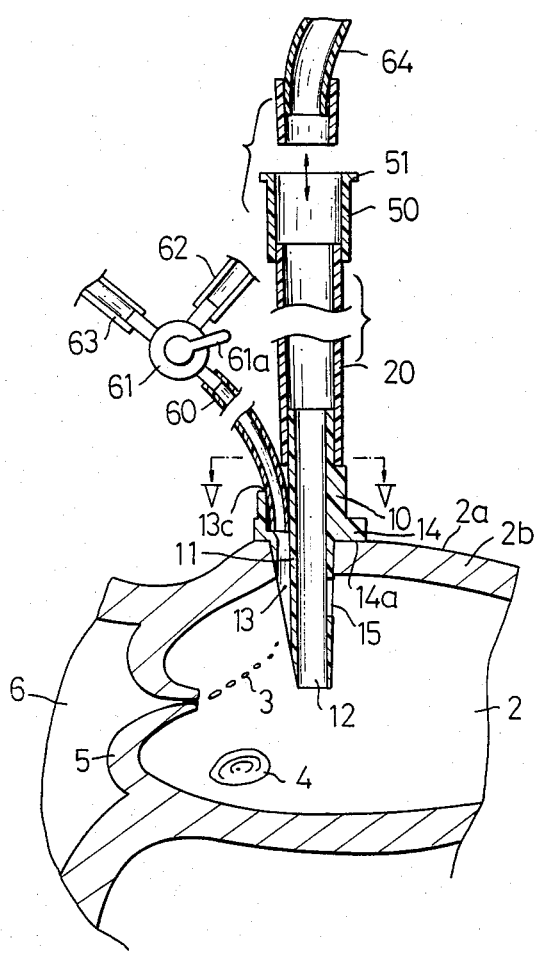

The tubage body 10 is formed into a tubular shape from a comparatively soft material such as polyvinyl chloride resin, and is provided therein with the above-mentioned conduits 12 and 13 separated from each other by a partition wall 11 extending in the longitudinal direction thereof, as shown in FIGS. 3 and 4. The conduit 12 has a diameter slightly greater than that of the conduit 13. The conduit 12 has an end opening 12a which is horizontal in the longitudinal cross-section of the tubage body 10, while the conduit 13 has an end opening 13b which is oblique in the longitudinal cross-section of the tubage body 10. The end opening 13b opens obliquely towards the end opening 12a of the conduit 12. The aforementioned stabbing guide needle 30 is received by the conduit 12 formed in the tubage body 10.

Figure 6:
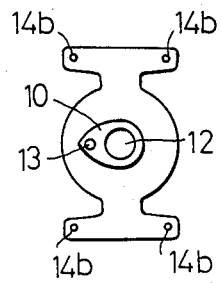
FIG. 6 is a schematic illustration of the tubage embodying the invention after the removal of a stabbing guide needle, as viewed from the open end thereof.

A flange 14 is formed substantially at the center of the tubage body 10. The flange portion 14 has an end surface 14a which contacts with the outer surface 2a of the aorta 2 to serve as a hemostasis member, when the aorta 2 is stabbed with the aortic tubage 1, as shown in FIGS. 2 to 4. To this end, the flange portion 14 is provided with four slots 14b as shown in FIG. 6. By sewing threads (not shown) passing through these slots 14b to the wall 2b of the aorta 2, it is possible to fix the aortic tubage 1.

A side hole 15, which is intended mainly for smoothing the final extraction of air bubbles in the chest surgery, is formed in the wall of the conduit 12 of larger diameter adjacent to the flange portion 14. More specifically, the position of the side hole 15 is selected such that the distance L between the aforementioned end surface 14a of the flange portion 14 and the open end 15a of the side hole 15 in the conduit 12 is equal to the distance M between the end surface 14a of the flange portion 4 and the open end 13a of the conduit 13. The distances L and M are equal to or greater than the wall thickness of the wall 2b of the aorta 2.

A tube 20 inserted and fixed at its one end to the conduit 12 at the base end portion of the tubage 10 is used for the injection of liquids such as cardiac muscle protective liquid, as well as for the extraction of air bubbles. This tube 20 is made of a flexible synthetic resin or a synthetic rubber, and is opened at its other end. A connector 50 fixed to the other end of the injection tube 20 is adapted to engage with a knob 31 which is provided on the end of the stabbing guide needle 30 which will be mentioned later. The engagement between the knob 31 and the connector 50 is achieved by attaining an engagement between engaging projections 51 projecting from the outer upper end of the connector 50. The illustrated embodiment incorporate two such engaging projections.

The stabbing guide needle 30 is a hollow needle made of stainless steel. In the normal retracted state of the stabbling guide needle 30, the end 30a thereof projects slightly out of the end opening 12a of the larger-diameter conduit 12 in the tubage 10, while most part of the needle 30 is received by the tubage body 10 and the tube 20. Therefore, a cap (not shown) is fitted to the end 30a of the stabbing guide needle 30 to protect the needle 30 before it is put into use.

In order to prevent blood from coming out of the hollow 30b, the stabbing guide needle 30 is contracted and restricted at any desired portion, e.g. mid portion 30c, so that the hollow 30b is materially contracted at this portion in a liquid tight manner. As stated before, the other end of the stabbing guide needle 30 is provided with the knob 31. In the state before the use, this knob 31 is retained by the connector 50 mentioned before so that the stabbing guide needle 30 is prevented from coming off from the conduit 12 and the tube 20.

A plug 40 fixed to the outer surface of the stabbing guide needle 30 is made of a hard resin material, and serves to prevent the blood from flooding out through the gap between the tube 20 and the stabbing guide needle 30 when the needle 30 is gradually withdrawn from the tubage body 10 and the tube 20, after stabbing the wall 2b of the aorta. Namely, when the stabbing guide needle 30 is withdrawn from the tube 20, the plug 40 ascends while making a liquid-tight contact with the inner surface of the tube 20.

A description will be made hereinunder as to how the aortic tubage shown in FIG. 1 is actually used, with specific reference to FIGS. 2 to 4. In advance to the use, a tube 60 is fitted into the base end opening 13c of the conduit 13 in the tubage body 10, while connecting the other end of the tube 60 to a three-way cock 61, so as to form a bubble extraction circuit 62 and an artery pressure measuring line 63.

Then, the surgeon stabs an upper portion of the aorta 2 of the patient, i.e. the portion near the surgeon's eyes, with the stabbing guide needle 30 of the aortic tubage 1, and sews the threads passing through the slots 14b in the flange portion 14 to the wall 2b of the aorta 2, thereby to fix the tubage 1 to the aorta 2.

Subsequently, the stabbing guide needle 30 is gradually extracted from the tubage body 10 and the tube 20, until the end 30a of the stabbing guide needle 30 takes the position shown in FIG. 3, i.e. substantially to the mid portion of the tube 20. Then, the flood passage is tentatively shut off by, for example, a clamp 55. Then, the stabbing guide needle 30 is perfectly withdrawn from the tubage body 10 and the tube 20. Thereafter, the connector 50 is connected to the circuit 64 for injecting cardiac muscle protective liquid. Reference numerals 4,5 and 6 denote, respectively, a coronary opening, aortic valve and a left ventricle.

Assume here that a liquid such as cardiac muscle protective liquid is charged into the base portion of the aorta through an injection circuit 64 connected to the connector 50, and the change-over member 61a of the three-way cock 61 to bring the conduit 13 into communication with the circuit 62 which has been in the ventilated condition, so that the air bubbles 3 in the aorta 2 are removed by sucking. In this case, the air bubbles 3 are introduced into the tube 60 through the conduit 13. It is recalled that the distance M (see FIG. 1) between the end surface 14a of the flange portion 14 and the open end 13a of the conduit 13 is equal to or slightly greater than the thickness of the wall 2b of the aorta 2, so that it is possible to introduce the ascending air bubbles 3 into the tube 60 without fail.

After the completion of the sucking of the air bubbles 3 through the circuit 62, the aforementioned change-over member 61a of the three-way cock 61 is operated to provide a connection between the aortic pressure measuring line 63 and the conduit 13 while closing the circuit 62, thereby to permit the measurement of the blood pressure in the artery.

As will be understood from the foregoing description, the tubage of the invention permits the extraction of air bubbles and the injection of cardiac muscle protective liquid to be conducted simultaneously. In addition, it is possible to effect the measurement of the artery pressure after the completion of extraction of air bubbles. In the described embodiment, the conduit 12 has an inside diameter of about 2 mm and imposes a certain resistance against the flow of the injected liquid. The aforementioned side hole 15 is provided to minimize the pressure loss of the injected liquid. According to the invention, however, the final extraction of air bubbles in the chest surgery operation can be conducted by making an efficient use of the conduit 12 because the distance L between the end surface 14a of the flange portion 14 and the open end 15a of the side hole 15 is equal to or only slightly greater than the thickness of the wall 2b of the aorta 2. In fact, it is possible to extract the air bubbles more securely and smoothly through the conduit 12 than through the side hole 15.

In the embodiment described hereinbefore, the tube 60 is inserted into the base end opening 13c of the conduit 13 in the tubage body 10. This, however, is not essential and it is possible to adopt the following arrangement advantageously. Namely, it is possible to fix one end of the tube 60 to the base end opening 13c of the conduit 13 by means of an adhesive while attaching beforehand the three-way cock 61 to the other end of the tube 60.

Figure 7:
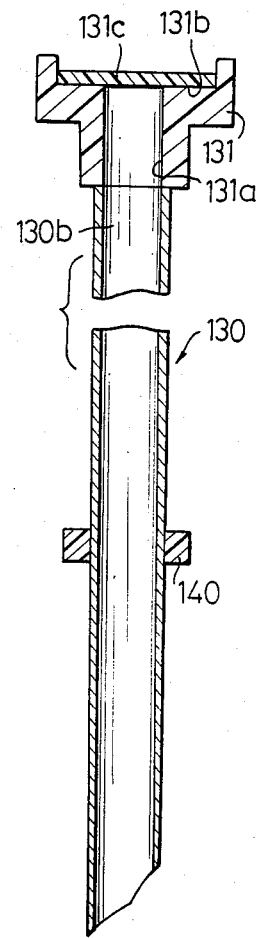
FIG. 7 is a sectional view of another example of the stabbing guide needle incorporated in the tubage of the invention.

FIG. 7 shows another example of the stabbing guide needle.

The stabbing guide needle 130 shown in FIG. 7 also is a hollow stainless steel needle as in the case of the foregoing embodiment. A knob 131, fixed to the rear end of the stabbing guide needle 130, has a through hole 131a which is in communication with the hollow 130b of the stabing guide needle 130. A bacterial filtration filter 131c fits in a recess 131b formed in an upper portion of the knob 131 in such a manner as to cover the through hole 131a. This filter 131c is a known one made of an non-woven cloth of polyester resin, which is permeable to air but impermeable to bacteria. A plug 140 made of a soft synthetic resin and fixed to the outer wall of the hollow 130b of the needle 130 constitutes a sealing means as in the case of the foregoing embodiment.

When this stabbing guide needle 130 is used, the aortic blood flowing into the hollow 130b of the stabbing guide needle 130 at a pressure of about 120 mmHg does not permeate through the filter 131c so that it becomes unnecessary to provide a restriction at the intermediate portion of hollow of the stabbing guide needle. In addition, since the hollow 130b of the needle 130 is opened to the atmosphere, it is rather easy to stab the wall 2b of the aorta 2 with the stabbing guide needle 130.

As will be fully understood from the foregoing description, the tubage of the invention can be used for various purposes such as extraction of air bubbles in the heart cavity, injection of the cardiac muscle protective liquid, measurement of aortic pressure and so forth, in open heart surgery operations such as valvular substitution, repair of septum defect and so forth in the chest surgery to reduce the number of stabbing and cutting. This offers advantages not only for the patient but also for the surgeon because he can have a wide field of vision due to elimination of miscellaneous circuits and because the operation itself is made simple, which in turn affords the completion of the operation in a shorter period of time. Furthermore, the tubage of the invention minimizes the damaging of the wall of aorta during the operation advantageously.

It will thus be seen that the objects set forth above, among those other objects made apparent from the preceding description, are efficiently attained and, since certain changes may be made in the above construction without departing from the spirit and scope of the invention, it is intended that all matter contained in the above description or shown in the accompanying drawings shall be interrupted as illustrative and not in a limiting sense.

It is also to be understood that the following claims are intended to cover all of the generic and specific features of the invention hereindescribed, and all statements of the scope of the invention, which, as a matter of language, might be said to fall therebetween.

What is claimed is:

1. A tubage for use in an intubation which comprises:
   a first tubular body having a first conduit and a second conduit formed respectively to extend in the longitudinal direction of said first tubular body, a flange portion extending in the direction substantially perpendicular to said longitudinal direction, and a side hole formed to open to the first conduit at a predetermined distance from said flange portion;
   a flexible second tubular body connected at its one end to one end of said first conduit so as to communicate with said first conduit;
   a hollow needle removably received by said first conduit and by said flexible second tubular body; and
   a liquid seal means provided between the inner surface of said second tubular body and the outer surface of said hollow needle.

2. A tubage as set forth in claim 1, wherein said first conduit has a greater diameter than said second conduit.

3. A tubage as set forth in claim 1, wherein said flange portion is provided at substantially mid point in the longitudinal direction of said first tubular body, said substantially mid point containing said first and second conduits.

4. A tubage as set forth in claim 3, wherein said flange portion is provided with a plurality of slots for passing a thread for sewing said first tubular body to a wall of artery.

5. A tubage as set forth in claim 1, wherein the distance between the end surface of said flange portion and the edge of said side hole adjacent to said flange portion is substantially equal to the distance between said end surface of said flange portion and the open end of one end opening of said second conduit.

6. A tubage as set forth in claim 5, wherein said one open end of said second conduit is cut obliquely in the longitudinal section of said first tubular body.

7. A tubage as set forth in claim 5, further including a third tubular body connected at its one end to the other end of said second conduit to communicate the latter, and a three-way cock attached to the other end of said third tubular body.

8. A tubage as set forth in claim 1, wherein said liquid seal means comprises a plug member fitting the outer wall of said hollow needle.

9. A tubage as set forth in claim 1, further including a connector provided on the other end of said second tubular body and a knob provided on the rear end of said hollow needle and detachably connected to said connector on said other end of said second tubular body.

10. A tubage as set forth in claim 9, wherein said hollow needle is restricted in a fluid-tight manner at a predetermined portion along the length of said hollow needle.

11. A tubage as set forth in claim 1, wherein said hollow needle has a knob fixed to the rear end thereof, said knob having a through hole communicating with the hollow of said hollow needle, and a filter mounted thereon so as to cover said through hole.

* * * * *